US00PP08270P

United States Patent [19]

Bradford et al.

[11] Patent Number: Plant 8,270

[45] Date of Patent: Jun. 22, 1993

[54] ALMOND TREE (SAVANA)

[76] Inventors: Lowell G. Bradford, 12439 E. Savana Rd.; Norman G. Bradford, 11875 E. Savana Rd., both of Le Grand, Calif. 95333

[21] Appl. No.: 840,772

[22] Filed: Feb. 24, 1992

[51] Int. Cl.[5] ..... A01H 5/00

[52] U.S. Cl. ..... Plt./32.2

[58] Field of Search ..... Plt./32.2

*Primary Examiner*—James R. Feyrer

[57] ABSTRACT

The present invention relates to an almond tree and more particularly to a new and distinct variety broadly characterized by a medium size, moderately vigorous, spreading, hardy, very late blooming, very productive, and regular bearing tree whose nuts mature under the ecological conditions described approximately the second week in September. The nuts have thin hulls and are very well sealed to protect kernels that are uniformly large in size, light in color, and flat in shape.

1 Drawing Sheet

BACKGROUND OF THE VARIETY

In a continuing effort to improve the quality of shipping fruits and nuts, we, the inventors, typically hybridize a large number of nectarine, peach, plum, apricot, cherry, and almond seedlings each year. The present invention relates to a new and distinct variety of almond tree, which has been denominated varietally as "Savana". The present variety was selected in 1982 by use in a cultivated area of our experimental orchard at Bradford Farms near Le Grand, Calif., in Merced County (San Joaquin Valley). This hybrid seedling resulted from using Nonpareil Almond (unpatented) as the selected seed parent and an unnamed late blooming almond seedling as the selected pollen parent. Subsequent to origination of the present variety of almond tree, we asexually reproduced it by budding and grafting, and such reproduction of plant and nut characteristics were true to the original plant in all respects.

The tree of the present variety is most similar to that of its seed parent, the Nonpareil, by being moderately vigorous and spreading, but is very distinguished therefrom by blooming two weeks later. The nuts produced by the present variety are also similar to the Nonpareil nuts by having kernels that are large in size, light in color, and flat in shape, but are distinguished therefrom by maturing two weeks later, by having a tightly closed inner shell to protect the kernels from insects, and by having thin hulls that are easily removed from the in-shell nuts and/or kernels by mechanical airlegs during processing.

In comparison to the Texas Almond (unpatented) variety, the blooming period of the present variety is one week later but the harvest period is two weeks earlier.

DRAWING

The accompanying color photograph exhibits nuts in hull, exposed hulls, nuts out of hull, kernels out of shell, and leaves, all typical of the instant variety.

POMOLOGICAL CHARACTERISTICS

Referring now more specifically to the pomological characteristics of this new and distinct variety of almond tree, the following has been observed under the ecological conditions prevailing near LeGrand, Merced County (San Joaquin Valley), California, and was developed at the harvest stage on Sep. 15, 1991. All major color code designations are by reference to the Inter-Society Color Council, National Bureau of Standards. Common color names are also used occasionally.

TREE

Size: Medium.
Vigor: Medium.
Growth: Spreading and open.
Form: Vase formed.
Hardiness: Hardy.
Production: Very productive.
Bearing: Regular bearer.
Trunk:
- *Size.*—Medium.
- *Texture.*—Shaggy.
- *Bark color.*—Brownish gray [64. brGy].
- *Lenticles.*—Numerous. Color: Light Brown[57. l.Br]. Average Size: 5/16" [7.9 mm].

Branches:
- *Size.*—Medium.
- *Texture.*—Smooth.
- *Color.*—1st Year Wood: Moderate yellow green [120. m.YG]. Older Wood: Moderate yellowish brown [77. m.yBr].
- *Lenticels.*—Numerous, very small.

Leaves:
- *Size.*—Medium. Average length: 3⅞" [98.4 mm.]. Average width: 1 5/16" [33.3 mm.].
- *Thickness.*—Medium.
- *Form.*—Lanceolate.
- *Apex.* —Acuminate.
- *Base.*—Acute.
- *Surface.*—Smooth.
- *Color*—Dorsal Surface: Dark olive green [126. d.0lG]. Ventral Surface: Moderate olive green [125. m.0lG].
- *Margin.*—Serrate.
- *Venation.*—Pinnately net veined.
- *Petiole.*—Average Length: 9/16" 14.3 mm.]. Average Thickness: 1/16" [1.6 mm.]. Dorsal Color: Moderate yellow green [120. m.YG]. Ventral Color: Light yellow green [119.l.YG].
- *Stipules.*—Few. Average Length: 3/16" [4.8 mm.].
- *Glands.*—Numbers: Mostly 2 or 3 per leaf. Position: Mostly alternately positioned on petiole and base of blade. Size: Small. Form: Globose. Color: Light yellow green [119. l.YG].

Flower buds:

*Hardiness.*—Hardy.

*Size.*—Medium.

*Length.*—Medium.

*Form.*—Free.

*Surface.*—Pubescent.

Flowers:

*Blooming period.*—Approximately 2 weeks later than Nonpareil.

*Blooming duration.*—Medium.

*Type.*—Self-sterile, must be cross pollinated by other late blooming varieties.

*Amount of bloom.*—Heavy.

*Size.*—Large.

*Color.*—white [263. White].

HULL

Outer surface: Smooth, Pubescent.

Form: Uniform, symmetrical.

*Longitudinal section form.*—Oval.

Average thickness: 1/16" [1.6 mm] when dry.

Flesh: Tough, but brittle when dry.

Suture: A sharp crack prior to splitting.

External color: Grayish greenish yellow [105. gy.gY].

Dehiscence: Opens freely.

Splitting: Complete along suture.

Adherence: Hulls are easily removed from nuts by mechanical hullers.

Density: Hulls are relatively light and readily removed from inshell nuts and kernels by mechanical airlegs during hulling and shelling processes.

Nut cavity: Oval

*Surface.*—Rough.

*Color when first opened.*—Pale yellow green [121. p.YG.].

*Color when dry.*—Light orange yellow [70.l.OY].

NUT

Size:

*Average length.*—1¼" [31.8 mm.].

*Average width.*—¾" [19.1 mm.].

*Average thickness.*—9/16" [14.3 mm.].

*Average weight.*—14.7 nuts per ounce [1.9 grams per nut].

Form: Oval.

Shell:

*Color.*—Light yellowish brown [76.l.yBr].

*Average wall thickness.*—1/16" [1.6 mm.].

*Pits.*—Small, numerous.

*Outer shell.*—Crumbling.

*Inner shell.*—Thin, brittle, well sealed.

Base: Straight.

Apex: Acute.

Stem: Medium.

*Average length.*—¼" [6.4 mm.].

*Average diameter.*—3/16" [4.8 mm.].

Wing: Thin, tapered toward base.

*Average protrusions.*—⅛" [3.2 mm.].

Inner surface: Smooth.

*Color.*—Light yellowish brown [76.l.yBr].

KERNEL

Size: Medium to large.

*Average length.*—1" [25.4 mm.].

*Average width.*—½" [12.7 mm.].

*Average thickness.*—5/16" [7.9 mm.].

*Average weight.*—23.9 nuts per ounce [1.2 grams per nut].

Form: Uniform, symmetrical.

*Longitudinal section form.*—Oblong.

*Transverse section form.*—Elliptically flattened.

Base: Slightly oblique, shouldered on one side, rounded on the other.

Apex: Acute.

Surface: Slightly wrinkled, slightly pubescent.

*Pellicle color.*—Moderate orange yellow [71. m.OY].

*Veins.*—Numerous deep yellowish brown [75. deep yBr] veins extending longitudinally from the base to the apex with some branching.

Number of doubles: Very few on most years.

Number of defective kernels: Very few on most years.

Flavor: Bland to slightly sweet.

Astringency: None.

Quality: Very good.

Viable: Yes.

Blanchable: Yes.

Percentage of kernel to nut: 61.6%.

CULTURAL CHARACTERISTICS

Resistance to insects: Much more resistant to kernel insect damage than Nonpareil due to its very well sealed inner shell.

Susceptibility to budfailure: Observance of budfailure has occurred, but these incidents have been rare.

Resistance to other diseases: No unusual susceptibilities noted.

Susceptibility to frost: No unusual susceptibility noted, but the exposure duration is shorter than most varieties due to the late onset of blooming.

Although the new variety of almond tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of almond tree, substantially as illustrated and described, which is most similar to its seed parent, the Nonpareil (unpatented), by being moderately vigorous and spreading in growth and by producing large, flat, light colored kernels, but is distinguished therefrom and an improvement thereon by appearing to be a heavier and more consistent producer, by blooming and maturing two weeks later, by producing nuts that have tightly closed inner shells to protect the kernels from insects, and by having thin hulls that are easily removed from the inshell nuts and kernels by mechanical airlegs during processing.

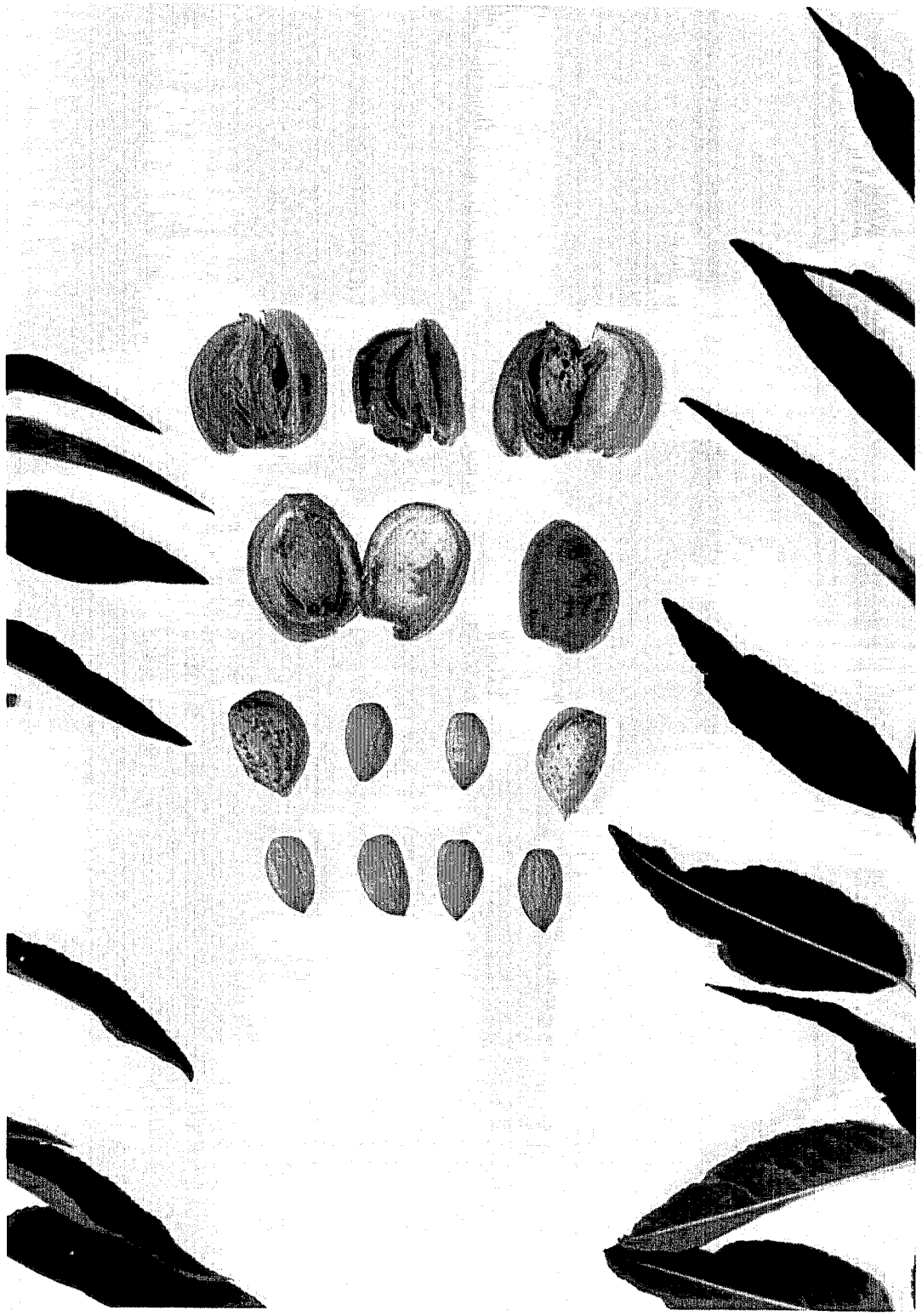

* * * * *